United States Patent [19]

Muszak et al.

[11] Patent Number: 4,795,710

[45] Date of Patent: Jan. 3, 1989

[54] MOUNTING OF ANALYZER SAMPLE TRAY

[75] Inventors: Martin F. Muszak, Rochester; James D. Shaw, Hilton, both of N.Y.

[73] Assignee: Eastman Kodak Company, Rochester, N.Y.

[21] Appl. No.: 160,626

[22] Filed: Feb. 26, 1988

[51] Int. Cl.⁴ .................. C12M 1/00; A47G 29/00
[52] U.S. Cl. ............................... 435/287; 422/64; 211/78; 211/131; 211/163
[58] Field of Search ............. 435/291, 310, 287; 206/499, 562, 563, 564; 250/576; 356/246; 211/78, 131, 144, 163, 70, 77; 422/64, 100, 104; D24/31, 32

[56] References Cited

U.S. PATENT DOCUMENTS

| D. 287,634 | 1/1987 | Carr et al. .................. D24/31 |
| D. 289,199 | 4/1987 | Tag et al. ................... D24/31 |
| 3,605,829 | 9/1971 | Genese et al. ............... 422/64 |
| 4,287,155 | 9/1981 | Tersteeg et al. ............. 422/64 |

FOREIGN PATENT DOCUMENTS 1116157 6/1988 United Kingdom ........... 206/563

Primary Examiner—Samuel Scott
Assistant Examiner—Noah Kamen
Attorney, Agent, or Firm—Dana M. Schmidt

[57] ABSTRACT

A tray-hanging device is disclosed for trays used in an analyzer. It comprises a rotatable platform having a raised annular lip configured to engage a first part of the tray along a first side of the lip, and a depending skirt portion positioned above the platform, configured to receive the weight of a second part of the tray pressing on a side of the skirt portion opposite to the engaged first side of the lip, the lip further including centering notches shaped to cooperate with ribs on the tray to prevent relative respective rotation of tray and device, and to properly locate the tray on the platform.

4 Claims, 4 Drawing Sheets

MOUNTING OF ANALYZER SAMPLE TRAY

BACKGROUND OF THE INVENTION

In conventional analyzers using so-called "dried" test elements, at least some designs provide the patients' serum for analysis in cups mounted on a rotating tray. The tray comes in segments, such as quarter segments of an annular ring, that are mounted and dismounted onto a rotating platform. The analyzer operator removes a tray segment from the platform, mounts serum-containing cups along the outer rim portion of the tray, and then remounts the tray onto the platform.

Conventionally such tray segments are interlocked with the platform at two locations. One location, a post on the platform close to the platform axis, engages a hole in an inner rim of the tray quarter-segment. At a second location, a rib on the outer edge of the platform engages a corresponding slot adjacent the outer rim of the tray segment.

Such a design requires a careful machining of the engaging post-and-hole configurations, and of the engaging rib-and-slot configurations. In addition, they require some attention on the part of the user so that the tray is properly remounted without spilling the contents of the cups. The user also must be cautious to not bend or damage the interacting parts, lest the interlock of pin-and-hole, or rib-and-slot, be prevented or rendered difficult.

It is true that these factors of manufacture and use have been manageable, and many analyzers are successfully being used with such features. However, there has been a need, prior to this invention, to simplify the mounting of the tray on its platform. That is, a better mounting has been sought that would minimize the criticality of parts tolerances, as well as the care required by the user.

SUMMARY OF THE INVENTION

We have constructed a tray-hanging device that overcomes the manufacturing and use problems noted above.

More specifically, there is provided a tray-hanging device for trays holding containers of liquid in an analyzer, the device comprising:

a rotatable platform having a raised annular lip configured to engage a first part of a tray along a first side of the lip, and a depending skirt portion positioned above the platform, configured to receive the weight of a second part of a tray pressing on a side of the skirt portion opposite to the engaged first side of the lip, the lip further including centering notches shaped to cooperate with ribs on a tray to prevent relative respective rotation of tray and device, and to properly locate a tray on the platform.

Thus, it is an advantageous feature of the invention that a tray-hanging device is provided for use in an analyzer, that does not require careful machining or maintenance of post or rib features that engage openings in a tray.

It is another advantageous feature of the invention that such a device is provided that readily accepts the mounting of a tray with less care than previously required.

Other advantageous features will become apparent upon reference to the following Description of the Preferred Embodiments, when read in light of the attached drawings.

DESCRIPTION OF PREFERRED EMBODIMENTS

The invention is described herein in connection with the mounting of preferred trays that hold containers of patient serum and also disposable nozzles used to aspirate and dispense the serum. In addition, the invention is useful regardless of the contents of the containers on the tray, the shape of the containers, and whether or not nozzles are also mounted on the tray.

Directions such as "up", "down", "horizontal" and the like are hereafter referred to in the context of the respective orientations during use.

Figure 1:
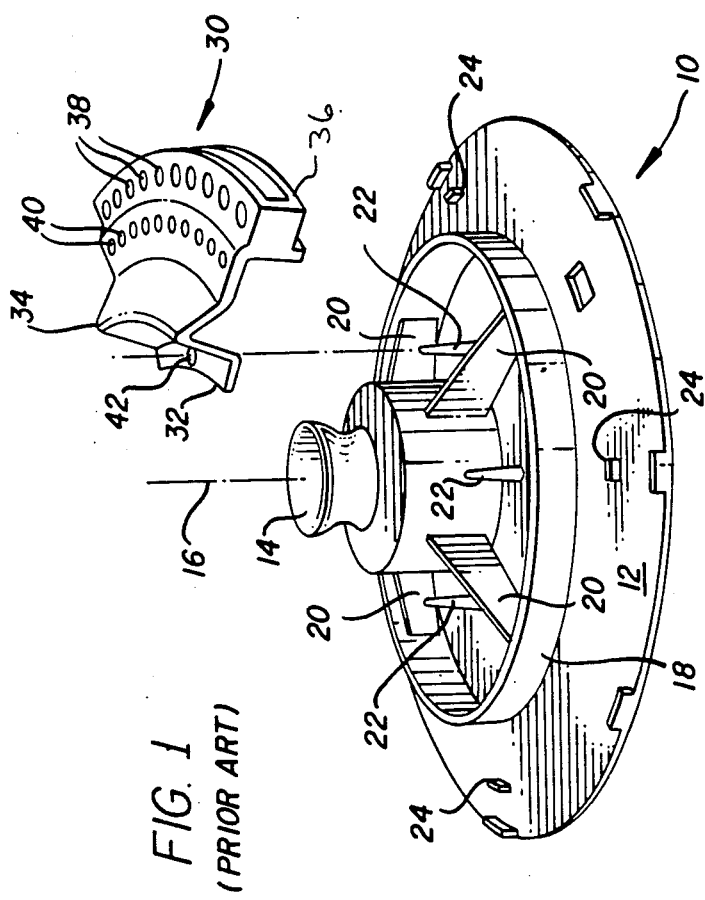
FIG. 1 is a partial, exploded isometric view of a tray-hanging device available in the prior art.

As noted in the "Background", an analyzer such as the Kodak "Ektachem 700" TM analyzer conventionally mounted and the containers of patient serum and dispensing nozzles, on a tray segment 30 removably mounted on a rotatable platform 10, FIG. 1. Platform 10 comprises a base disc 12, a knob 14 centered on axis of rotation 16, and a vertical ring 18. The space between knob 14 and ring 18 is divided into 4 quadrants by buttresses 20. Within each quadrant, a vertical pin 22 projects upwardly. Radially outwardly of the ring 18, but aligned with pin 22 and axis 16, is a rib 24.

The tray comprises 4 quarter segments 30 that complete an annular ring, when mounted on platform 10. One segment is illustrated. Each segment has an inner lower lip 32, a shoulder 34 spaced outwardly and extending upwardly from lip 32, and an outer rim portion 36. Portion 36 is apertured at 38 to receive containers of patients' liquid, and at location 40 that is interior from apertures 38, to receive dispensing nozzles. An aperture 42 in lip 32 is constructed to closely fit over pin 22, and a slot under outer rim portion 36 (not shown) closely fits over rib 24.

Figure 2:
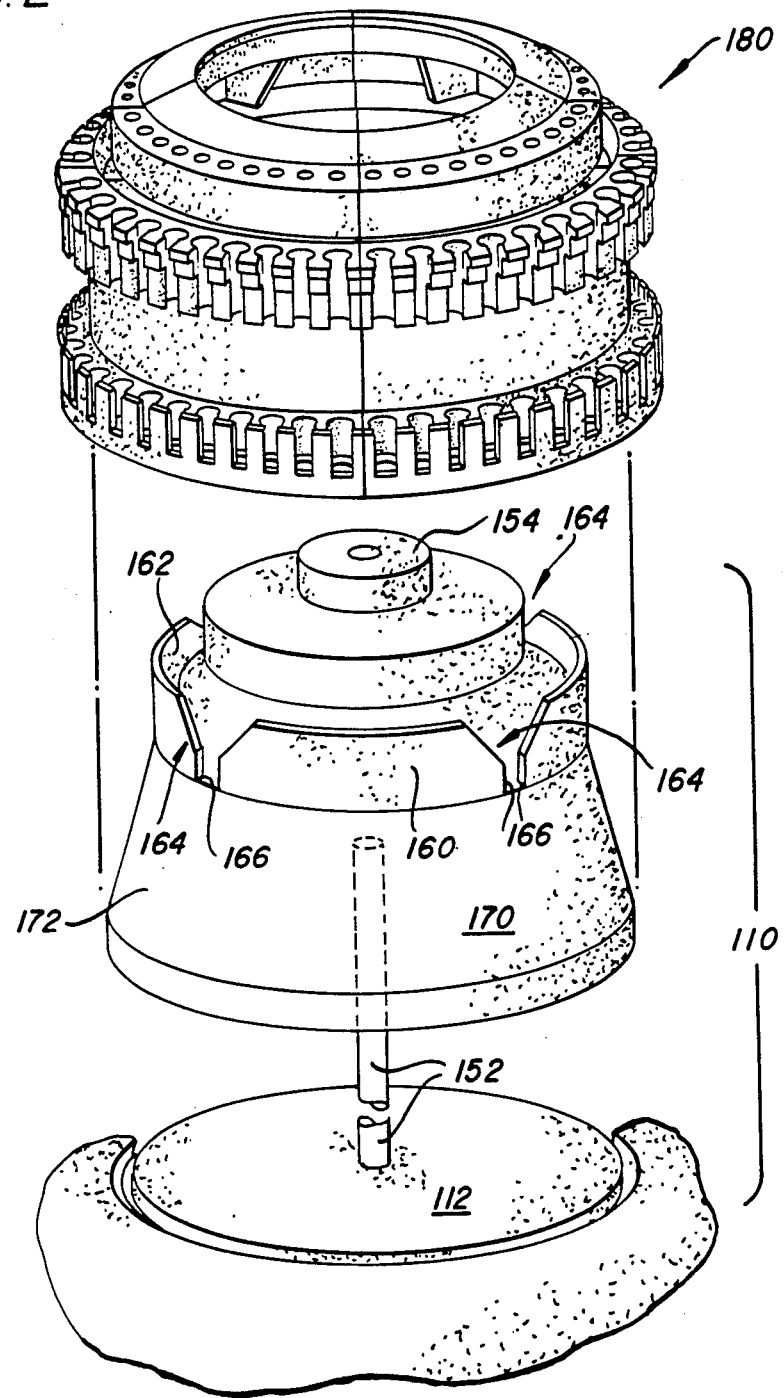
FIG. 2 is an exploded, partially fragmentary, isometric view of a tray-hanging device constructed in accord with the invention.
Figure 3:
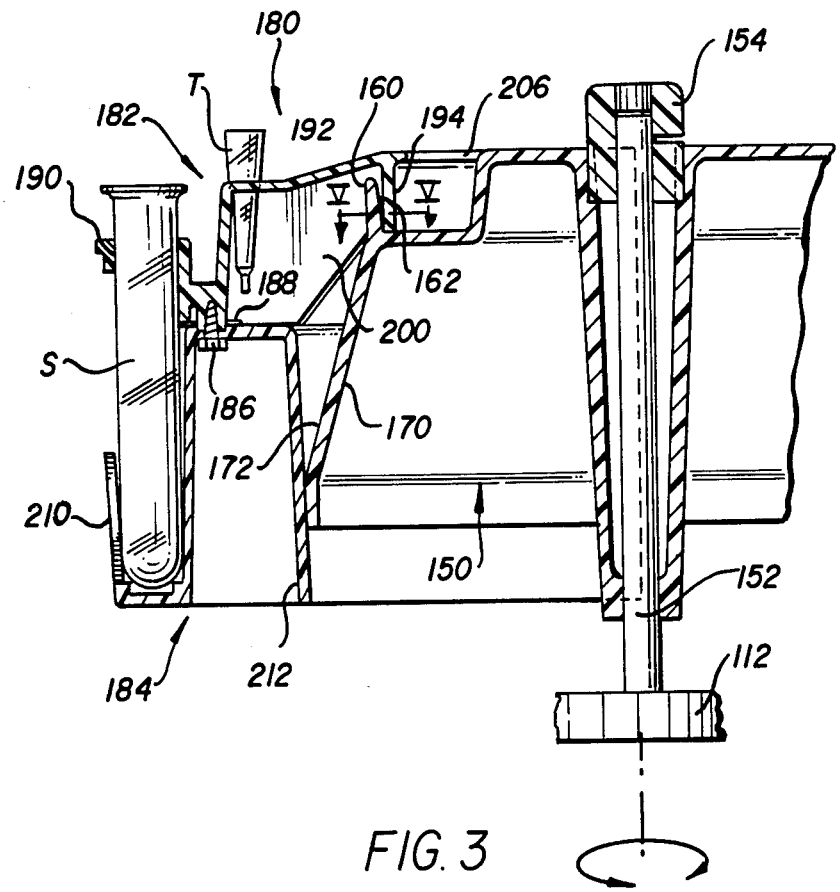
FIG. 3 is a fragmentary, elevational view in section of the engagement of a tray using this invention.
Figure 4:
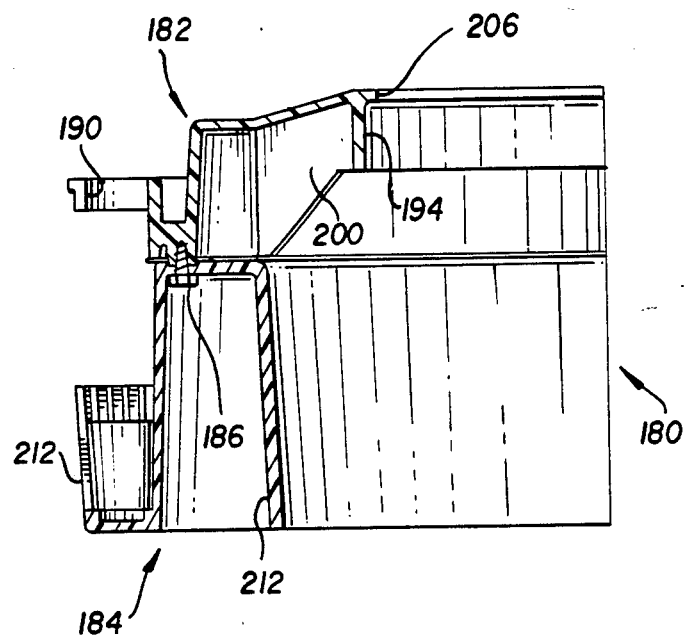
FIG. 4 is a fragmentary, elevational view in section of just the tray of FIG. 3.

In accord with the invention, the tray and its support have been modified as shown in FIGS. 2 through 4. The support 110 comprises a base disk 112 and a conical portion 150, FIG. 3, that is secured to a vertical post 152 that is fixed to disk 112, as by a nut 154, FIGS. 2 and 3. Portion 150 includes a raised annular lip 160 that extends around post 152. The inside surface 162 of lip 160, FIG. 3, is constructed to bear the weight of a depending lip portion 194 of trays 180. To locate and hold the tray in proper circumferential position on platform 110, lip 160 has a plurality of V-shaped notches 164 that preferably are positioned with a vertically upward opening. The V-shape guides tray ribs into place. Preferably the notches are four in number, angularly spaced around post 152 each to receive a tray. At the bottom of each notch 164 is a vertical portion formed by parallel sides 166, that lock a tray in place.

Depending from lip 160 is a skirt portion 170, FIGS. 2 and 3, having an outer surface 172 that is opposite to the inside surface 162 of lip 160. This surface bears the weight of the lower portion of tray 180.

Trays 180 are preferably provided in four segments, FIG. 2, as before. Most preferably they comprise an upper portion 182 and a lower portion 184, for ease in molding. They are then screw-attached at 186, preferably with an annular strip 188 of fabric or elastomer that projects outwardly to frictionally engage a sample tube, FIG. 3.

Upper portion 182 is provided with the conventional apertures 190 and 192 to receive sample containers "S" and disposable tips "T", respectively. A downwardly-depending annular lip 194 is designed to bear against surface 162 of lip 160 of conical portion 150.

Figure 5:
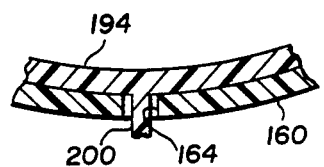
FIG. 5 is a fragmentary sectional view taken along the line V—V of FIG. 3.

To angularly locate each of the upper tray segment portions 182 properly on conical portion 150, a rib or gusset 200 extends downwardly from the tray and radially inwardly towards post 152, FIG. 3. Ribs 200 fit into notches 164 and 166, as can best be seen in FIG. 5.

A horizontally extending lip 206 extends from lip 194, and provides a grasping edge for holding trays 180.

Lower portion 184 of the trays 180 completes the holding of containers S. An upwardly extending shoulder 210 is shaped with apertures to receive the lower end of containers S. Complementary skirt portion 212 is shaped to bear on skirt portion 170 at surface 172.

The assembly of the apparatus will be readily apparent from the preceding. The support conical portion 150 is attached by nut 154, to post 152. The four tray segments 180 are then each loaded with appropriate sample container S, and disposable tips T used by the dispensing portion of the analyzer to aspirate sample from containers S. Once loaded, a tray is grasped by holding onto lip 206, and placed over lip 160 so that upper lip 194 of the tray is inside lip 160 (FIG. 3). The tray is rotatably adjusted until rib 200 is above a notch 164. The tray is lowered so that rib 200 centers in notch 164. Gravity is then used to cause rib 200 to lock in place in notch portion 166, FIG. 5, with skirt 212 of the tray bearing on skirt portion 170 at surface 172, of support 110, FIG. 3. Removal of the tray is followed by reversing the procedure.

It will be readily apparent from the preceding that the tolerances of notches 164 and 166, and of the corresponding ribs 200, need not be as carefully observed as in the conventional prior art construction. Furthermore, each tray segment has only one interlocking member with the tray support, rather than two.

The invention has been described in detail with particular reference to preferred embodiments thereof, but it will be understood that variations and modifications can be effected within the spirit and scope of the invention.

What is claimed is:

1. A tray-hanging device for trays holding containers of liquid in an analyzer, the device comprising:
    a rotatable platform having a raised annular lip configured to engage a first part of a tray along a first side of the lip,
    and a depending skirt portion positioned above said platform, configured to receive the weight of a second part of a tray pressing on a side of said skirt portion opposite to said engaged first side of said lip,
    said lip further including centering notches shaped to cooperate with ribs on a tray to prevent relative respective rotation of tray and device, and to properly locate a tray on said platform.

2. A tray-hanging device as defined in claim 1, wherein said notches are V-shaped to guide a tray into position.

3. A tray-hanging device as defined in claim 1, wherein said notches are positioned with a vertical, upward opening when in use, so that a tray can be located by gravity pulling a tray rib into the notch.

4. A tray-hanging device as defined in claim 1, wherein said centering notches are four in number, evenly spaced around said lip.

* * * * *

UNITED STATES PATENT AND TRADEMARK OFFICE
CERTIFICATE OF CORRECTION

PATENT NO. : 4,795,710

DATED : January 3, 1989

INVENTOR(S) : Muszak, Martin F. and Shaw, James D.

It is certified that error appears in the above-identified patent and that said Letters Patent is hereby corrected as shown below:

Col. 2, line 28 should read:
  --the like are hereinafter referred to in the context of the--
Col. 2, line 32 should read:
  --ally mounted the containers of patient serum and--
Col. 3, line 33 should read:
  --containers S, and disposable tips T used by the dispens- --

Signed and Sealed this

Twelfth Day of December, 1989

*Attest:*

JEFFREY M. SAMUELS

*Attesting Officer*   *Acting Commissioner of Patents and Trademarks*